US008865458B2

(12) United States Patent
Ramsey et al.

(10) Patent No.: US 8,865,458 B2
(45) Date of Patent: *Oct. 21, 2014

(54) SPECIMEN COLLECTION AND ASSAY CONTAINER

(71) Applicant: Alere Switzerland GmbH, Zug (CH)

(72) Inventors: James T. Ramsey, Virginia Beach, VA (US); Larry Hartselle, Virginia Beach, VA (US)

(73) Assignee: Alere Switzerland GmbH, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/776,172

(22) Filed: Feb. 25, 2013

(65) Prior Publication Data

US 2013/0287650 A1    Oct. 31, 2013

Related U.S. Application Data

(63) Continuation of application No. 12/477,107, filed on Jun. 2, 2009, now Pat. No. 8,394,626, which is a continuation of application No. 10/336,204, filed on Jan. 4, 2003, now Pat. No. 7,560,272.

(51) Int. Cl.
   *C12M 1/34*   (2006.01)
   *G01N 33/558*   (2006.01)
   *A61B 10/00*   (2006.01)

(52) U.S. Cl.
   CPC .............. *B10L 3/508* (2013.01); *G01N 33/558* (2013.01); *Y10S 435/81* (2013.01); *Y10S 436/805* (2013.01); *A61B 10/007* (2013.01); *A61B 10/0096* (2013.01); *Y10S 436/81* (2013.01)

USPC ..... 435/288.5; 422/401; 422/417; 435/288.4; 435/810; 436/805; 436/810

(58) Field of Classification Search
   CPC ........... G01N 33/5302; G01N 33/5304; B01L 3/502; B01L 2400/00
   See application file for complete search history.

(56) References Cited

U.S. PATENT DOCUMENTS

| 228,031 A | 5/1880 | Broughton et al. |
| 424,982 A | 4/1890 | Hidden et al. |
| 645,430 A | 3/1900 | Smelker et al. |

(Continued)

FOREIGN PATENT DOCUMENTS

| EP | 0250137 | 12/1987 |
| EP | 0291194 | 11/1988 |

(Continued)

OTHER PUBLICATIONS

"Is he using drugs?" ACON Product brochure, 2003.

(Continued)

*Primary Examiner* — Chris L Chin
(74) *Attorney, Agent, or Firm* — DLA Piper LLP (US)

(57) ABSTRACT

The present invention includes but is not limited to a specimen collection device that includes a chamber capable of collecting a specimen, a specimen passage slot, a reservoir, a reservoir seal, and a test device. A sample or specimen added to the chamber flows through the specimen passage slot into the reservoir. Flow into the reservoir may be limited by the reservoir seal. The test device positioned within the reservoir detects the presence or concentration of an analyte within the sample or specimen.

15 Claims, 1 Drawing Sheet

(56) References Cited

U.S. PATENT DOCUMENTS

| | | |
|---|---|---|
| 711,452 A | 10/1902 | Meyer et al. |
| D140,925 S | 4/1945 | Christner et al. |
| 3,000,540 A | 9/1961 | Wheeler |
| 3,658,216 A | 4/1972 | Schwartzman |
| 3,687,333 A | 8/1972 | Burnett et al. |
| 3,688,942 A | 9/1972 | Mitchell et al. |
| 3,723,064 A | 3/1973 | Liotta |
| 3,837,518 A | 9/1974 | Gach |
| 3,951,748 A | 4/1976 | Devlin |
| 3,990,850 A | 11/1976 | Friedman et al. |
| 3,990,853 A | 11/1976 | Godin |
| 3,991,055 A | 11/1976 | Godin et al. |
| 4,015,400 A | 4/1977 | Choksi et al. |
| 4,024,976 A | 5/1977 | Acton |
| 4,055,501 A | 10/1977 | Cornell |
| 4,063,460 A | 12/1977 | Svensson |
| 4,087,326 A | 5/1978 | Kereluk |
| 4,087,332 A | 5/1978 | Hansen |
| 4,111,329 A | 9/1978 | Lampman |
| D250,129 S | 10/1978 | Skinner |
| 4,133,639 A | 1/1979 | Harte |
| 4,165,018 A | 8/1979 | Giggard |
| 4,177,930 A | 12/1979 | Crisci |
| 4,190,175 A | 2/1980 | Allen |
| 4,205,043 A | 5/1980 | Esch et al. |
| 4,211,749 A | 7/1980 | Kantner |
| 4,237,234 A | 12/1980 | Meunier |
| 4,244,916 A | 1/1981 | Guigan |
| D258,311 S | 2/1981 | Peterson |
| 4,270,921 A | 6/1981 | Graas |
| 4,275,149 A | 6/1981 | Litman et al. |
| 4,298,345 A | 11/1981 | Sodickson et al. |
| 4,299,916 A | 11/1981 | Litman et al. |
| 4,301,139 A | 11/1981 | Feingers et al. |
| 4,313,734 A | 2/1982 | Leuvering |
| 4,323,536 A | 4/1982 | Columbus |
| 4,338,094 A | 7/1982 | Elahi |
| 4,361,537 A | 11/1982 | Deutsch et al. |
| 4,362,697 A | 12/1982 | Tabb et al. |
| 4,366,241 A | 12/1982 | Tom et al. |
| 4,376,110 A | 3/1983 | David et al. |
| 4,391,904 A | 7/1983 | Litman et al. |
| 4,394,944 A | 7/1983 | Rech |
| 4,421,244 A | 12/1983 | Van Melle |
| 4,425,438 A | 1/1984 | Bauman et al. |
| 4,426,451 A | 1/1984 | Columbus |
| 4,435,504 A | 3/1984 | Zuk et al. |
| 4,443,896 A | 4/1984 | Porat et al. |
| 4,446,232 A | 5/1984 | Liotta |
| 4,462,510 A | 7/1984 | Steer et al. |
| 4,474,892 A | 10/1984 | Murad et al. |
| 4,476,993 A | 10/1984 | Krout |
| 4,485,938 A | 12/1984 | Williams |
| 4,493,432 A | 1/1985 | Smith |
| 4,512,493 A | 4/1985 | Von Holdt |
| 4,517,288 A | 5/1985 | Giegel et al. |
| 4,535,057 A | 8/1985 | Dreesman et al. |
| 4,646,926 A | 3/1987 | Agbay et al. |
| 4,657,027 A | 4/1987 | Paulsen |
| 4,659,678 A | 4/1987 | Forrest et al. |
| 4,666,863 A | 5/1987 | Edwards et al. |
| D290,136 S | 6/1987 | Ball et al. |
| 4,673,657 A | 6/1987 | Christian |
| 4,678,757 A | 7/1987 | Rapkin et al. |
| 4,680,270 A | 7/1987 | Mitsumaki et al. |
| 4,700,860 A | 10/1987 | Li |
| 4,703,017 A | 10/1987 | Campbell et al. |
| 4,711,364 A | 12/1987 | Letica |
| 4,718,571 A | 1/1988 | Bordner |
| 4,722,458 A | 2/1988 | Van Dal |
| 4,725,406 A | 2/1988 | Compton et al. |
| 4,740,468 A | 4/1988 | Weng et al. |
| 4,752,448 A | 6/1988 | Wells et al. |
| 4,769,215 A | 9/1988 | Ehrenkranz |
| D299,744 S | 2/1989 | Bauer |
| 4,806,311 A | 2/1989 | Greenquist |
| 4,806,487 A | 2/1989 | Akers et al. |
| 4,807,771 A | 2/1989 | Roy et al. |
| 4,813,563 A | 3/1989 | Ogden et al. |
| 4,827,944 A | 5/1989 | Nugent |
| 4,837,168 A | 6/1989 | de Jaeger et al. |
| 4,852,560 A | 8/1989 | Hermann, Jr. et al. |
| 4,853,335 A | 8/1989 | Olsen et al. |
| 4,855,240 A | 8/1989 | Rosenstein et al. |
| 4,856,667 A | 8/1989 | Thompson |
| 4,857,453 A | 8/1989 | Ullman et al. |
| 4,859,610 A | 8/1989 | Maggio |
| 4,886,184 A | 12/1989 | Chamourian |
| 4,900,663 A | 2/1990 | Wie et al. |
| 4,909,933 A | 3/1990 | Carter et al. |
| 4,923,680 A | 5/1990 | Nelson |
| 4,938,927 A | 7/1990 | Kelton et al. |
| 4,943,522 A | 7/1990 | Eisinger et al. |
| 4,952,517 A | 8/1990 | Bahar |
| 4,954,452 A | 9/1990 | Yost et al. |
| 4,959,324 A | 9/1990 | Ramel et al. |
| 4,960,691 A | 10/1990 | Gordon et al. |
| 4,961,351 A | 10/1990 | Gerken |
| 4,966,302 A | 10/1990 | Hjordie |
| 4,973,549 A | 11/1990 | Khanna et al. |
| 4,981,786 A | 1/1991 | Dafforn et al. |
| 4,987,085 A | 1/1991 | Allen et al. |
| 5,002,198 A | 3/1991 | Smith |
| 5,006,474 A | 4/1991 | Horstman et al. |
| 5,028,535 A | 7/1991 | Buechler et al. |
| 5,069,878 A | 12/1991 | Ehrenkranz |
| 5,073,484 A | 12/1991 | Swanson et al. |
| 5,075,078 A | 12/1991 | Osikowicz et al. |
| 5,079,142 A | 1/1992 | Coleman et al. |
| 5,082,626 A | 1/1992 | Grage, Jr. |
| 5,085,988 A | 2/1992 | Olson |
| 5,089,391 A | 2/1992 | Buechler et al. |
| 5,092,478 A | 3/1992 | La Pierre |
| 5,096,837 A | 3/1992 | Fan et al. |
| 5,111,947 A | 5/1992 | Patterson |
| 5,115,934 A | 5/1992 | Nelson |
| 5,116,576 A | 5/1992 | Stanley |
| 5,118,607 A | 6/1992 | Bignami et al. |
| 5,119,830 A | 6/1992 | Davis |
| 5,119,831 A | 6/1992 | Robin et al. |
| 5,120,643 A | 6/1992 | Ching et al. |
| 5,135,199 A | 8/1992 | Cross et al. |
| 5,141,850 A | 8/1992 | Cole et al. |
| 5,141,875 A | 8/1992 | Kelton et al. |
| 5,156,952 A | 10/1992 | Litman et al. |
| 5,165,572 A | 11/1992 | Bath |
| 5,185,127 A | 2/1993 | Vonk |
| 5,186,367 A | 2/1993 | Hickerson |
| 5,186,897 A | 2/1993 | Eason et al. |
| 5,202,268 A | 4/1993 | Kuhn et al. |
| 5,207,340 A | 5/1993 | Cochrane |
| 5,232,835 A | 8/1993 | Litman et al. |
| 5,238,652 A | 8/1993 | Sun et al. |
| RE34,394 E | 9/1993 | Bunting |
| 5,252,496 A | 10/1993 | Kang et al. |
| D341,663 S | 11/1993 | Coulter |
| 5,260,193 A | 11/1993 | Olson |
| 5,266,497 A | 11/1993 | Imai et al. |
| 5,270,166 A | 12/1993 | Parsons et al. |
| 5,271,517 A | 12/1993 | Bowers |
| 5,275,785 A | 1/1994 | May et al. |
| 5,279,330 A | 1/1994 | Debush |
| 5,294,015 A | 3/1994 | Landis |
| 5,296,347 A | 3/1994 | LaMotte, III |
| 5,308,775 A | 5/1994 | Donovan et al. |
| 5,354,692 A | 10/1994 | Yang et al. |
| 5,356,782 A | 10/1994 | Moorman et al. |
| 5,381,918 A | 1/1995 | Dahl |
| 5,395,754 A | 3/1995 | Lambotte et al. |
| 5,399,486 A | 3/1995 | Cathey et al. |
| 5,403,551 A | 4/1995 | Galloway et al. |
| 5,415,994 A | 5/1995 | Imrich et al. |
| 5,416,000 A | 5/1995 | Allen et al. |
| 5,424,193 A | 6/1995 | Pronovost et al. |

(56) References Cited

U.S. PATENT DOCUMENTS

| | | |
|---|---|---|
| 5,429,804 A | 7/1995 | Sayles |
| 5,435,970 A | 7/1995 | Mamenta et al. |
| D361,842 S | 8/1995 | Nazareth et al. |
| 5,451,504 A | 9/1995 | Fitzpatrick et al. |
| D366,938 S | 2/1996 | Shartle et al. |
| 5,489,414 A | 2/1996 | Schreiber et al. |
| 5,500,350 A | 3/1996 | Baker et al. |
| 5,504,013 A | 4/1996 | Senior |
| D369,868 S | 5/1996 | Nazareth et al. |
| 5,523,051 A | 6/1996 | Gibson |
| 5,523,055 A | 6/1996 | Hansen et al. |
| 5,543,115 A | 8/1996 | Karakawa |
| 5,591,645 A | 1/1997 | Rosenstein |
| 5,595,187 A | 1/1997 | Davis |
| 5,597,532 A | 1/1997 | Connolly |
| 5,601,191 A | 2/1997 | Meador |
| 5,602,040 A | 2/1997 | May et al. |
| 5,622,871 A | 4/1997 | May et al. |
| 5,641,012 A | 6/1997 | Silversides |
| 5,641,637 A | 6/1997 | Hudak et al. |
| 5,654,162 A | 8/1997 | Guire et al. |
| 5,656,503 A | 8/1997 | May et al. |
| 5,658,531 A | 8/1997 | Cope et al. |
| D384,971 S | 10/1997 | Kawan |
| D388,167 S | 12/1997 | Caradonna et al. |
| 5,712,172 A | 1/1998 | Huang et al. |
| D390,667 S | 2/1998 | Nazareth |
| 5,714,389 A | 2/1998 | Charlton et al. |
| 5,716,778 A | 2/1998 | Weng et al. |
| 5,728,587 A | 3/1998 | Kang et al. |
| 5,739,041 A | 4/1998 | Nazareth et al. |
| 5,744,366 A | 4/1998 | Kricka et al. |
| D395,708 S | 6/1998 | Shartle et al. |
| 5,770,460 A | 6/1998 | Pawlak et al. |
| 5,785,044 A | 7/1998 | Meador et al. |
| 5,794,107 A | 8/1998 | Russell |
| 5,807,752 A | 9/1998 | Brizgys et al. |
| 5,843,691 A | 12/1998 | Douglas et al. |
| 5,846,835 A | 12/1998 | Sisbarro et al. |
| D404,812 S | 1/1999 | Cipkowski |
| 5,869,006 A | 2/1999 | Fanning et al. |
| 5,874,216 A | 2/1999 | Mapes |
| 5,877,028 A | 3/1999 | Chandler et al. |
| 5,897,840 A | 4/1999 | Owens, Jr. et al. |
| 5,904,898 A | 5/1999 | Markart |
| 5,916,815 A | 6/1999 | Lappe |
| 5,922,283 A | 7/1999 | Hsu |
| 5,922,533 A | 7/1999 | Vallari et al. |
| 5,922,615 A | 7/1999 | Nowakowski et al. |
| 5,929,422 A | 7/1999 | Lappe |
| 5,932,430 A | 8/1999 | Larka et al. |
| 5,939,252 A | 8/1999 | Lennon et al. |
| 5,939,272 A | 8/1999 | Buechler et al. |
| 5,939,331 A | 8/1999 | Burd et al. |
| 5,942,442 A | 8/1999 | Di Cesare et al. |
| 5,962,333 A | 10/1999 | Incorvia et al. |
| 5,965,453 A | 10/1999 | Skiffington et al. |
| 5,965,458 A | 10/1999 | Kouvonen et al. |
| 5,975,373 A | 11/1999 | Forsberg |
| 5,976,469 A | 11/1999 | Davis |
| 5,976,895 A | 11/1999 | Cipkowski |
| 5,981,293 A | 11/1999 | Charlton |
| 5,989,921 A | 11/1999 | Charlton et al. |
| 5,994,145 A | 11/1999 | Stave et al. |
| 6,008,056 A | 12/1999 | Thieme |
| D420,141 S | 2/2000 | Casterlin |
| 6,020,147 A | 2/2000 | Guire et al. |
| 6,025,203 A | 2/2000 | Vetter et al. |
| 6,057,151 A | 5/2000 | Greenwood et al. |
| 6,087,184 A | 7/2000 | Magginetti et al. |
| D430,303 S | 8/2000 | Cipkowski |
| 6,096,563 A | 8/2000 | Hajizadeh et al. |
| 6,140,136 A | 10/2000 | Lee |
| D434,494 S | 11/2000 | Wilkinson et al. |
| 6,153,439 A | 11/2000 | Johnson |
| 6,165,416 A | 12/2000 | Chandler |
| 6,168,758 B1 | 1/2001 | Forsberg et al. |
| 6,170,719 B1 | 1/2001 | Wilkinson et al. |
| 6,171,261 B1 | 1/2001 | Niermann et al. |
| 6,174,006 B1 | 1/2001 | Burt |
| 6,187,269 B1 | 2/2001 | Lancesseur et al. |
| 6,194,224 B1 | 2/2001 | Good et al. |
| 6,210,909 B1 | 4/2001 | Guirguis |
| 6,234,241 B1 | 5/2001 | Elmore |
| 6,235,241 B1 | 5/2001 | Catt et al. |
| 6,248,598 B1 | 6/2001 | Bogema |
| 6,271,046 B1 | 8/2001 | Chandler |
| 6,277,646 B1 | 8/2001 | Guirguis et al. |
| 6,284,195 B1 | 9/2001 | Lai et al. |
| 6,291,178 B1 | 9/2001 | Schneider |
| D449,524 S | 10/2001 | Kieras |
| 6,308,848 B1 | 10/2001 | Parrinello |
| 6,372,514 B1 | 4/2002 | Lee |
| 6,372,515 B1 | 4/2002 | Casterlin et al. |
| 6,375,896 B1 | 4/2002 | Wuske et al. |
| 6,375,897 B1 | 4/2002 | Bachand |
| 6,379,620 B1 | 4/2002 | Tydings et al. |
| 6,382,444 B1 | 5/2002 | Nyman |
| 6,403,383 B1 | 6/2002 | Casterlin et al. |
| 6,406,922 B2 | 6/2002 | Casterlin et al. |
| D464,141 S | 10/2002 | McMenamy et al. |
| 6,464,939 B1 | 10/2002 | Bachand et al. |
| 6,468,474 B2 | 10/2002 | Bachand et al. |
| D468,204 S | 1/2003 | Gittins et al. |
| D468,437 S | 1/2003 | McMenamy et al. |
| 6,514,769 B2 | 2/2003 | Lee |
| 6,548,019 B1 | 4/2003 | Lee et al. |
| 6,565,808 B2 | 5/2003 | Hudak et al. |
| 6,576,193 B1 * | 6/2003 | Cui et al. .................. 422/417 |
| 6,645,758 B1 | 11/2003 | Schnipelsky et al. |
| 6,663,831 B2 | 12/2003 | Konecke |
| 6,669,908 B2 | 12/2003 | Weyker et al. |
| 6,726,879 B2 | 4/2004 | Ng et al. |
| 6,730,268 B2 | 5/2004 | Lee et al. |
| 6,786,106 B2 | 9/2004 | Alley |
| 6,890,484 B2 | 5/2005 | Bautista et al. |
| 6,902,656 B2 | 6/2005 | Ouellet et al. |
| 6,955,099 B2 | 10/2005 | Goodin |
| 7,222,547 B2 | 5/2007 | Alley |
| 7,270,959 B2 | 9/2007 | Hudak |
| 7,560,272 B2 * | 7/2009 | Ramsey et al. ........... 435/288.4 |
| 8,394,626 B2 * | 3/2013 | Ramsey et al. ........... 435/287.1 |
| 2001/0004532 A1 | 6/2001 | Chandler |
| 2001/0008774 A1 | 7/2001 | May et al. |
| 2001/0021536 A1 | 9/2001 | Lee |
| 2001/0041368 A1 | 11/2001 | May et al. |
| 2002/0001854 A1 | 1/2002 | Lee |
| 2002/0004019 A1 | 1/2002 | Bachand et al. |
| 2002/0023482 A1 | 2/2002 | Pampinella |
| 2002/0031845 A1 | 3/2002 | Cipkowski |
| 2002/0052050 A1 | 5/2002 | Douglas et al. |
| 2002/0058031 A1 | 5/2002 | Tung et al. |
| 2002/0085953 A1 | 7/2002 | Parker |
| 2002/0096469 A1 | 7/2002 | Faulkner |
| 2002/0137231 A1 | 9/2002 | Cipkowski |
| 2002/0146346 A1 | 10/2002 | Konecke |
| 2002/0173047 A1 | 11/2002 | Hudak et al. |
| 2003/0004396 A1 | 1/2003 | Vanden Hock et al. |
| 2003/0007892 A1 | 1/2003 | Smith |
| 2003/0021727 A1 | 1/2003 | Weyker et al. |
| 2003/0021736 A1 | 1/2003 | Kang et al. |
| 2003/0022392 A1 | 1/2003 | Hudak |
| 2003/0027359 A1 | 2/2003 | Hudak et al. |
| 2003/0046814 A1 | 3/2003 | Knaup et al. |
| 2003/0129088 A1 | 7/2003 | Lee et al. |
| 2003/0129673 A1 | 7/2003 | Schwarz et al. |
| 2003/0129767 A1 | 7/2003 | Bautista et al. |
| 2003/0207466 A1 | 11/2003 | Po Lee |
| 2004/0053423 A1 | 3/2004 | LaBorde |
| 2004/0133128 A1 | 7/2004 | Guan et al. |
| 2004/0136877 A1 | 7/2004 | Kang et al. |
| 2004/0184965 A1 | 9/2004 | Smith |
| 2005/0008538 A1 | 1/2005 | Anderson et al. |
| 2005/0048670 A1 | 3/2005 | Wu et al. |

(56) References Cited

U.S. PATENT DOCUMENTS

| | | |
|---|---|---|
| 2005/0053519 A1 | 3/2005 | Smith |
| 2005/0106750 A1 | 5/2005 | Tung et al. |
| 2005/0106753 A1 | 5/2005 | Wu et al. |
| 2007/0092402 A1 | 4/2007 | Wu et al. |

FOREIGN PATENT DOCUMENTS

| | | |
|---|---|---|
| EP | 0183442 | 3/1990 |
| EP | 0250137 | 8/1992 |
| EP | 0291194 | 2/1994 |
| EP | 0284232 | 10/2002 |
| EP | 1284820 | 2/2003 |
| EP | 1028806 | 7/2003 |
| WO | WO 91/19980 | 12/1991 |
| WO | WO 97/33519 | 9/1997 |
| WO | WO 98/38917 | 9/1998 |
| WO | WO 00/29111 | 5/2000 |
| WO | WO 00/54024 | 9/2000 |
| WO | WO 00/62930 | 10/2000 |
| WO | WO 02/082040 | 10/2002 |
| WO | WO 02/095396 | 11/2002 |
| WO | WO 2004/038364 | 5/2004 |
| WO | WO 2005/006959 | 1/2005 |
| WO | WO 2005/007067 | 1/2005 |
| WO | WO 2005/008216 | 1/2005 |
| WO | WO 2005/023426 | 3/2005 |
| WO | WO 2005/050165 | 6/2005 |
| WO | WO 2005/050168 | 6/2005 |

OTHER PUBLICATIONS

"One step drug-of-abuse test," InTec Products, Inc. Product brochure, 2002.

ACON magazine advertisement, IVD Technology Magazine, p. 17 Mar./Apr. 2000.

ACON magazine advertisement, IVD Technology Magazine, p. 45 Nov./Dec. 1999.

ACON magazine advertisement, LabMedica Magazine, Jul./Aug. p. 14; Sep./Oct. p. 9; Nov./Dec. p. 23; 1999.

ACON OEM Product brochure, Aug. 2000.

\* cited by examiner

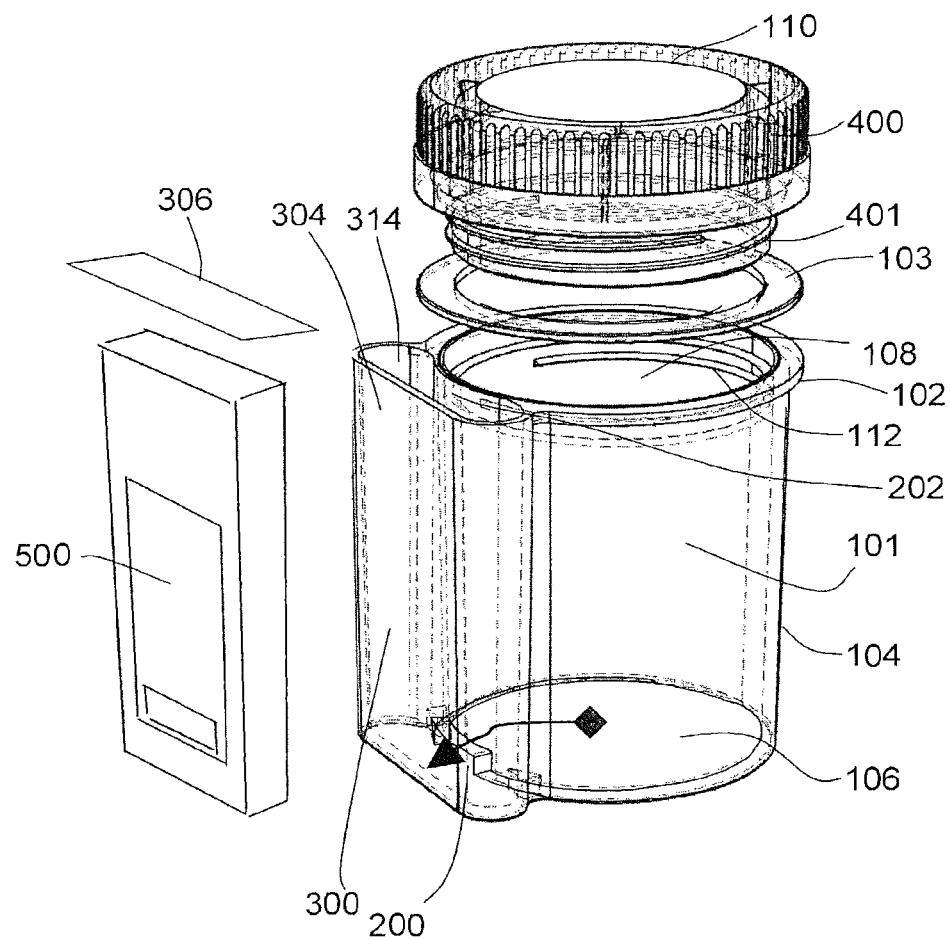

SPECIMEN COLLECTION AND ASSAY CONTAINER

CROSS-REFERENCE TO RELATED APPLICATIONS

This application is a continuation application of U.S. application Ser. No. 12/477,107 filed Jun. 2, 2009, now issued as U.S. Pat. No. 8,394,626; which is a continuation application of U.S. application Ser. No. 10/336,204 filed Jan. 4, 2003, now issued as U.S. Pat. No. 7,560,272. The disclosure of each of the prior applications is considered part of and is incorporated by reference in the disclosure of this application.

BACKGROUND OF THE INVENTION

1. Field of the Invention

The present invention relates generally to the field of sample collection and handling devices. More specifically the present invention relates to a sample collection and handling container having at least two chambers in fluid communication that regulate the flow of a sample to a test device.

2. Background Information

A variety of sample collection and assay devices for clinical or home use are available and described in the literature. These devices can be used for an assortment of purposes, including the detection of drugs or biological compounds such as glucose or hormones, antibodies or etiological agents. Many of these devices are complex in design and are difficult to use. Also, these devices are often manufactured and fabricated from relatively expensive materials. The present invention addresses these problems, and provides related benefits.

SUMMARY OF THE INVENTION

The present invention includes but is not limited to a specimen collection device that includes a chamber such that the chamber is capable of collecting or containing a specimen. The device also includes a reservoir and a reservoir seal such that the reservoir is capable of receiving a portion of the specimen from the chamber. The reservoir seal limits the amount of sample accessible to, the reservoir. The reservoir contains a test device for testing the specimen for an analyte. This chamber and the reservoir are in direct fluid communication through a specimen passage slot.

BRIEF DESCRIPTION OF THE DRAWINGS

FIG. 1 depicts one aspect of a specimen collection and assay container of the present invention, which includes, but is not limited to, a chamber 101, a reservoir 300, a specimen passage slot 200, a chamber seal 400 a reservoir seal 306 and a test device 500. The arrow illustrates the flow of a sample, such as urine, from the chamber 101, through the specimen passage slot 200 and into the reservoir 300.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Terms of orientation such as "up" and "down" or "upper" or "lower" and the like refer to orientation of the parts during use of the device. Where a term is provided in the singular, the inventors also contemplate the plural of that term. The nomenclature used herein and the laboratory procedures described below are those well-known and commonly employed in the art. As employed throughout the disclosure, the following terms, unless otherwise indicated, shall be understood to have the following meanings:

"Assaying" denotes the qualitative or quantitative testing a sample for an analyte. Assaying may incorporate an immunological test, a chemical test, an enzymatic test and the like. The present invention may assay for the presence or concentration of a variety of analytes such as but not limited to, a chemical, an organic compound, an inorganic compound, a metabolic product, a drug or a drug metabolite, an organism or a metabolite of such an organism, a nucleic acid, a protein, a hormone or a combination thereof. Assaying may involve comparing the results obtained against a positive or negative control as is common in the biochemical and immunological arts. When determining the concentration of an analyte the assay may also include at least one quantitative control to determine the amount of analyte present and may further include mathematical calculations such as comparing the amount of analyte to the volume within the collection container or reservoir.

An element of the present invention is "integral" to another element of the present invention when the two elements are manufactured or assembled as a single piece.

An element of the present invention is "separate" from another element of the present invention when the two elements are manufactured or provided as separate pieces.

A "reagent" can be any chemical, including organic compounds and inorganic compounds and combinations thereof. A reagent can be provided in gaseous, solid, or liquid form, or any combination thereof, and can be a component of a solution or suspension. A reagent preferably includes fluids, such as buffers useful in methods of detecting analytes in a sample or specimen, such as anticoagulants, diluents, buffers, test reagents, specific binding members, detectable labels, enzymes and the like. A reagent can also include an extractant, such as a buffer or chemical, to extract an analyte from a sample or specimen or a sample collection device. For example, a buffer can be used to extract analytes from the sample or specimen, such as LPS from bacteria.

An "assaying device" or "assay device" is a device for detecting the presence and/or concentration of an analyte in a sample or specimen. Assay devices of the present invention include but are not limited to lateral flow detection devices such as assay strip devices, and columns. In lateral flow detection devices the liquid sample or specimen moves through a matrix or material by lateral flow or capillary action, such as an immunochromatographic device. This migration generally involves passage through a sample application zone, a reagent zone and a detection zone. The sample application zone being the region of the lateral flow detection device which is contacted first by the sample, the reagent zone being the region in which particular reagents for the desired assay are positioned such that they may migrate with an analyte along the device and the detection zone being the region in which the results of the assay are visualized or determined. Commonly a mobilizable reagent such as a labeled antibody is provided in the reagent zone and an immobilized reagent is provided in the detection zone. A lateral flow detection device may be used in a substantially vertical or a substantially horizontal orientation or in an orientation substantially between vertical and horizontal. Preferably, neither a reagent zone nor a detection zone should contact the specimen or analyte unless the specimen or analyte migrates along the lateral flow detection device. Persons knowledgeable in the art commonly refer to a lateral flow detection device using terms such as "immunochromatographic," "dip sticks," "membrane technology" and "test strips."

"Analyte" is the compound or composition to be detected or measured. An analyte is generally capable of binding to a ligand, a receptor, or an enzyme. The analyte may be an antibody or antigen such as a protein or drug, or a metabolite. The precise nature of antigenic and drug analytes together with numerous examples thereof are disclosed in U.S. Pat. No. 4,299,916 to Litman, et al., particularly columns 16 to 23, and in U.S. Pat. No. 4,275,149, particularly columns 17 and 18, the disclosures of which are incorporated herein by reference in their entirety. Analytes can include antibodies and receptors, including active fragments or fragments thereof. An analyte can, include and analyte analogue, which is a derivative of an analyte, such as, for example, an analyte altered by chemical or biological methods, such as by the action of reactive chemicals, such as adulterants or enzymatic activity. An analyte can be but is not limited to a drug, a drug of abuse, a hormone, a protein, a nucleic acid molecule, an etiological agent, a specific binding member.

An "antibody" is an immunoglobulin, or derivative or active fragment thereof, having an area on the surface or in a cavity, which specifically binds to and is thereby defined as complementary with a particular spatial and polar organization of another molecule. Antibodies encompassed by the present invention include but are not limited to IgG, IgM, IgE, Fc, F(ab), F(ab)'2, light chain such as kappa and lambda, heavy chain fragments and the like. The antibody can be monoclonal or polyclonal and can be prepared by techniques that are well known in the art such as, for example, immunization of a host and collection of sera or hybrid cell line technology. Determining the proper antibody may be performed by performing binding assays known in the immunological arts such as an ELISA with the analyte of interest.

A "sample" or "specimen" refers to any material to be assayed for the presence and/or concentration of an analyte. Preferably, a sample is a fluid sample such as a liquid sample. Examples of liquid samples that may be assayed include bodily fluids such as but not limited to blood, serum, plasma, saliva, urine, ocular fluid, semen, and spinal fluid; water samples, such as samples of water from oceans, seas, lakes, rivers, and the like, or samples from home, municipal, or industrial water sources, runoff water or sewage samples; and food samples, such as milk or wine. Viscous liquid, semisolid, or solid specimens may be used to create liquid solutions, eluates, suspensions, or extracts that can be samples. For example, throat or genital swabs may be suspended in a liquid solution to make a sample. Samples can include a combination of liquids, solids, gasses, or any combination thereof, as, for example a suspension of lysed or unlysed cells in a buffer or solution. Samples can comprise biological materials, such as cells, microbes, organelles, and biochemical complexes. Liquid samples can be made from solid, semisolid or highly viscous materials, such as soils, fecal matter, tissues, organs, biological fluids or other samples that are not fluid in nature. For example, these solid or semisolid samples can be mixed with an appropriate solution, such as a buffer, such as a diluent or extraction buffer. The sample can be macerated, frozen and thawed, or otherwise extracted to form a fluid sample. Residual particulates may be removed or reduced using conventional methods, such as filtration or centrifugation.

Other technical terms used herein have their ordinary meaning in the art that they are used, as exemplified by a variety of technical dictionaries.

Introduction

As a non-limiting introduction to the breath of the present invention, the present invention includes several general and useful aspects, including but not limited to a specimen collection device that includes a chamber, a reservoir; a test device, a specimen passage slot and a reservoir seal. A sample added to the chamber passes through the specimen passage slot and enters the reservoir. The reservoir seal prevents excess sample from entering the reservoir. The sample enters the test device where the presence or concentration of an analyte is detected.

These aspects of the invention, as well as others described herein, can be achieved by using the articles of manufacture and compositions of matter described herein. To gain a full appreciation of the scope of the present invention, it will be further recognized that various aspects of the present invention can be combined to make desirable embodiments of the invention. In addition, a variety of other aspects and embodiments of the present invention are described herein.

Specimen Collection and Handling Device

With reference to FIG. 1, the specimen collection and assay container of the present invention includes, but is not limited to, a specimen collection and handling device that includes a chamber 101 such that the chamber 101 is capable of collecting or containing a specimen. The device also includes a reservoir 300 and a reservoir seal 306 such that the reservoir 300 is capable of receiving a portion of the specimen from the chamber 101. The reservoir seal 306 controls the amount of sample added to the reservoir 300 by generally downward forces generated by air or gasses which compress upon entry of the sample to the reservoir 300. The present invention optionally includes a specimen passage slot 200 functionally interposed between the chamber 101 and the reservoir 300 capable of transferring at least a portion of the specimen from the chamber 101 to the reservoir 300. The arrow in FIG. 1 illustrates one embodiment of the present invention demonstrating direct passage of a portion of a specimen from the chamber 101, through the specimen passage slot 200, into the reservoir 300.

Chamber

FIG. 1 shows one example of the chamber 101 of the specimen collection and assay container of the present invention. The chamber 101 can take the form of any number of different symmetrical configurations such as but not limited to cylindrical, convex, conical, elliptical, square, rectangular. Alternatively the chamber 101 may have an asymmetrical configuration such as but not limited to peanut shaped, kidney shaped or hybrid combinations thereof all with an inner surface and an outer surface. Furthermore, the size of the chamber 101 can be varied to meet the expected volumetric size of the specimen to be contained within the chamber 101.

The chamber 101 can have an upper opening 102 defined by the upper portion of the chamber 101 through which a specimen can be introduced into the interior of the chamber 101. In one embodiment of the present invention the chamber 101 can have a side wall 104, a bottom wall 106 and a specimen passage slot wall 202. The chamber side wall 104 and the specimen passage slot wall 202 may be substantially tapered either outwardly from the top to the bottom of the side wall 104 and the specimen passage slot wall 202 or inwardly from the top to the bottom of the side wall 104 and the specimen passage slot wall 202. The chamber bottom wall 106 can take the form of a substantially level wall or may be angled thereby directing flow towards the specimen passage slot 200. The chamber 101 optionally includes a chamber orifice 108 communicatively connecting the inside and the outside of the chamber 101.

The chamber 101 can optionally include a chamber seal 400 to facilitate the closure of the chamber upper opening 102. A non-exclusive list of mechanisms and methods that can be used to form seals useful in the present invention includes thermal welding, ultrasonic welding, vacuum sealing, compressive gaskets, screw-top lids, snap-top lids, compressive ring gaskets, gluing, compressive latch mechanisms, compressive spring mechanisms, snap couplings, bayonet couplings, zipping, hook and loop fasteners, screws, nails, bolting mechanisms, elastic band or bands, string and twine, wire, sliding mechanisms, plug or plugs, compressive clips, twist lids, epoxying, and tamper resistant mechanisms.

In another alternative embodiment of the present invention, there is included a tamper resistant seal or tamper evident seal to respectively prevent tampering with the chamber opening 102 or to facilitate the detection of tampering with the chamber opening 102. Tamper evident seals may be desirable to prevent tampering with the chamber 101 prior to or after inserting a sample into the chamber 101 and may be desirable to prevent tampering with the reservoir seal 306. Tamper resistant seals can be of various types including a strap seal of the kind containing a series of ratchet teeth arranged along the strap, with one end of the strap being secured to the outer surface of the chamber 101 and the other end of the strap being lockably inserted into a lid hingeably attached to the upper end of the chamber 101 so as to move the ratchet teeth sequentially past a resiliently deformable catch in the lid as described in U.S. Pat. No. 6,174,006. Other suitable tamper resistant and tamper evident seals are found in the use of foil seals, tape seals, locks, glue, epoxy, hot wax seals which are well known in the art. Another tamper resistant or tamper evident seal is found in the use of a plastic heat shrunk band typically disposed around a sealed lid or plastic heat shrunk membrane typically disposed over a closure or opening. Attempted removal of or tampering with the closure causes the band to separate from the closure skirt, providing an indication of the tampering. Another method of providing a tamper resistant seal or tamper evident seal is to securely seal the present invention including the closed chamber 101 inside another container. Yet another method of providing a tamper resistant seal is found in the use of a lid 110 with a series of sloped projections 401 which irreversibly and unidirectionally engages with a series of sloped projections 112 arrayed around the outer wall of the upper outer portion of the chamber 101. Preferably, the lid 110 with a series of sloped projections 401 irreversibly and unidirectionally engages with a series of sloped projections 112 arranged around the inner wall of the upper interior portion of the chamber 101, as shown in FIG. 1.

In a further alternative embodiment of the invention the chamber seal 400 can include a screw-lid 110. Such an embodiment can include an array of external threads 112 unitary with and in proximity to the open top 102 portion of the chamber side wall 104. The threads can rotatably mate with similar threads 401 on lid 110 and thus hermetically seal the chamber 101 from outside contamination or adulteration and prevent the leakage or discharge of the contents of the chamber 101 during normal use conditions. The chamber seal 400 may optionally include an O-ring 103 which may prevent unwanted leakage. In another embodiment of the present invention, the chamber seal 400 includes a snap-lid. Snap-on plastic hinged closures of the type mentioned above well known in the art and come in a large number of various designs. Conventional plastic snap-lid closures mainly include two basic elements. For one, they have a main joint around which the pivot movement of the lid in relation to the lower part takes place, and they furthermore have one or several intermediate elements creating the snap effect. Such intermediate elements can be in the form of straps, triangles or angled flexible springs or even longitudinally deformable tension spring elements. Snap-lid closures which can be incorporated into the present invention are found and described in the following U.S. Pat. No.: 3,688,942 by Mitchell et al.; U.S. Pat. No. 4,165,018 by Giggard; U.S. Pat. No. 4,177,930 by Crisci; U.S. Pat. No. 4,421,244 by Van Melle; U.S. Pat. No. 4,476,993 by Krout; U.S. Pat. No. 4,718,571 by Bordner; U.S. Pat. No. 4,966,302 by Hjordie; U.S. Pat. No. 5,271,517 by Bowers; U.S. Pat. No. 5,294,015 by Landis; U.S. Pat. No. 5,381,918 by Dahl; U.S. Pat. No. 228,031 by Broughton; U.S. Pat. No. 424,982 by Hidden; U.S. Pat. No. 3,837,518 by Gach; U.S. Pat. No. 4,024,976 by Acton; U.S. Pat. No. 4,111,329 by Lampman; U.S. Pat. No. 4,190,175 by Allen; U.S. Pat. No. 4,493,432 by Smith; U.S. Pat. No. 4,512,493 by Von Holdt; U.S. Pat. No. 4,646,926 by Agbay et al.; U.S. Pat. No. 4,700,860 by Li; U.S. Pat. No. 4,711,364 by Letica; U.S. Pat. No. 4,718,571 by Bordner; U.S. Pat. No. 4,807,771 by Roy et al.; U.S. Pat. No. 4,886,184 by Chamourian; U.S. Pat. No. 5,002,198 by Smith; U.S. Pat. No. 5,092,478 by La Pierre; U.S. Pat. No. 5,111,947 by Patterson; U.S. Pat. No. 5,115,934 by Nelson; U.S. Pat. No. 5,207,340 by Cochrane; and U.S. Pat. No. 5,271,517 by Bowers which are herein incorporated by reference in their entirety.

As mentioned above, the size of the chamber 101 can be varied to meet or exceed the expected volumetric size of the specimen to be contained within the chamber 101. As a lower limit, the chamber volume should be sufficiently large to transfer an adequate volume for a test device 500, and should take into account any adhesive forces that may exist between the materials of construction and the sample which may reduce transfer of the sample to the reservoir 300. As an upper limit, the chamber 101 should be sufficiently small that when the chamber 101 is full, the forces exerted from a sample entering the reservoir 300 do not overload the reservoir 300 and therefore overload the particular test device or test strip. As a general guideline, the chamber 101 size may be manufactured to accommodate specimen volumes greater than about 1.0 milliliter, 0.1 milliliter, 0.01 milliliter, 0.001 milliliter or about 0.0001 milliliter and may be manufactured to accommodate volumes less than about 1 milliliter, 5 milliliters, 10 milliliters, 50 milliliters, 100 milliliters, 250 milliliters, 500 milliliters, 750 milliliters, 1,000 milliliters or about 2,000 milliliters. The volume required for a gaseous sample may require a smaller or greater volume than the volume required for a liquid sample.

It is also desirable, but not required, for there to be one or more labels or some other scribe-able or scribed surface or surfaces on the chamber 101 or reservoir 300 on which to print, write or display information. Such label or treated surface can be positioned on the outer, wall of the chamber 101 and the printing, writing or display can be accomplished by gluing, imprinting, texturing, scribing, etching, surface treating, impregnating, painting, screen printing, dyeing, coloring, embossing, or other suitable method. Alternatively, such treatments can be applied to the interior of the chamber. In one embodiment of the present invention, a self-adhesive pre-printed label is affixed to the outer wall of the chamber 101. In another alternative embodiment of the present invention, this self-adhesive label can have a surface which accepts written notation through the use of a pen, pencil or marker or any such writing device. In preferred embodiments of the present invention, the chamber 101 is substantially transparent, such that the chamber can be seen through.

As will become apparent, the present invention utilizes traditional methods of construction known in the mechanical arts or medical device construction arts. The materials from which the chamber 101 can be manufactured are varied. The possible materials include metal, silicon, glass, ceramic, plastic and synthetic and natural polymers and combinations and mixtures thereof. In one embodiment of the present invention, the chamber 101 can be manufactured from a polypropylene composition using an appropriate manufacturing method such as pressure injection molding or machining. With the use of other materials, there will necessarily be the need to utilize other suitable methods of manufacturing such as milling, casting, blowing, and spinning however these are well known in the mechanical arts and medical device construction.

As mentioned previously, the chamber 101 can be of almost any conceivable shape which retains fluids. It may be desirable to construct the chamber side wall 104 such that it is perpendicular to the bottom wall 106 or tapered inward or outward from top to bottom. The taper can range from about 1 to about 50 degrees off perpendicular, A desirable angle for the chamber side wall 104 may be between about 1 and 45 degrees off perpendicular. Alternatively, the chamber side wall 104 angle may be tapered from about 1 to about 35 degrees off perpendicular. In another embodiment of the present invention the chamber side wall 104 is tapered off about 30 degrees off perpendicular.

Reservoir and Reservoir Seal

The specimen collection device can include at least one reservoir 300. The reservoir 300 is configured to accept a portion of the specimen delivered from the chamber 101 through the specimen passage slot 200 and to allow the testing of such portions of the specimen for the analyte. The reservoir 300 must be sufficiently large that a test device 500 or test strip may be positioned within the reservoir and should be of a size that air or a gas trapped within the reservoir 300 forces the sample to a desirable level and prevents the test device 500 or test strip from being overloaded with a sample. Various shapes and sizes may be tested for their applicability by observing the height of a sample within the sealed reservoir 300. The test device 500 may be inserted in the reservoir during assembly by the manufacturer or at the point of care. To facilitate assembly, the top part 304 of the reservoir 300 may contain an opening 314 such as a slot to permit the functional engagement of a test strip or test device 500. Alternatively the test device may be inserted between two halves of a reservoir and fused closed. IU another alternative embodiment of the present invention, the opening 314 of the reservoir 300 is hermetically sealed or sealed air tight with a reservoir seal 306. Suitable reservoir seals can include, but are not limited to, plugs, films and self-adhesive seals made of paper, wax paper, plastic materials, thin metal films, metallicized plastic or paper, and may further include a select scored cover made integral with the adjacent reservoir 300 material which scoring allows the selectively scored cover area to be removed through breakage of the scored areas. Optionally the reservoir seal 306 is not removable from the reservoir 300 after insertion of the test device 500 into the reservoir 300. When the test device 500 is removable, it may be desirable to empty the remaining sample from the chamber 101 or block the specimen passage slot 200 thereby preventing an influx of sample into the reservoir 300 once the seal 306 is removed. In further preferred embodiments, the test device 500 is permanently sealed inside the reservoir 300 by the reservoir seal 306.

As with the chamber 101, the reservoir 300 can be manufactured using traditional manufacturing techniques known in the mechanical and manufacturing arts and may be constructed with various materials. These materials can include metal, silicon, glass, ceramic, plastic and synthetic and natural polymers or any combination thereof. In one embodiment of the invention, the reservoir 300 can be manufactured from a polypropylene composite using an appropriate manufacturing method such as pressure injection molding or machining. In another embodiment the reservoir 300 is constructed from polystyrene using similar methods known in the art of plastics construction. Methods of manufacturing can include but are not limited to milling, casting, blowing, and spinning. In preferred embodiments of the present invention, the reservoir 300 is substantially transparent, such that a sealed test device 500 may be visualized. As will be further discussed later, the reservoir 300 may be constructed separately from the chamber 101 or may be constructed from a single mould. When constructed separately, the reservoir 300 may be joined with the chamber 101 by the manufacturer or at the point of care or prior to use. Assembly may be performed by aligning the reservoir with the chamber and may involve permanently affixing the reservoir to the chamber such as by using glue, interlocking surfaces such as snaps and the like. Alternatively, the reservoir may be reversibly affixed to the chamber however when this is the case, it may be desirable to remove airy remaining sample from the chamber prior to disengaging the reservoir 300 from the chamber 101 or utilize a method whereby the specimen passage slot 200 is blocked when the reservoir 300 is not engaged.

In one embodiment of the present invention, the reservoir 300 will accept and engage either a test card or a test device 500 such as one or more test strips in a testably functional arrangement so as to permit the contact of the portion of the specimen with the appropriate sampling region or regions on the bottom of the test card or test device 500. In another embodiment, the test card or test device 500 is permanently sealed inside the reservoir 300 by the reservoir seal 306.

Specimen

The specimen collection device of the present invention is capable of collecting specimens including liquid specimens of the nature and character as described above in the definition portion of this disclosure. Alternatively, the specimen collection device can collect other types of specimens. For example, the specimen may be composed of fine powdery materials such as talc, carbon black, pharmaceutical preparations, or gases such as argon or methane. Additional specimens can include atmospheric specimens that can be tested for particulates or radioactive isotopes such as radon.

In an alternative embodiment of the present invention the specimen to be collected is a biological specimen. Such biological specimens include but are not limited to a sample from a subject such as an animal or a human. A sample from a subject can be of any appropriate type, such as a sample of fluid, tissue, organ or a combination thereof. The biological specimen can also be a sample of other biological material, such as food, including food such as material derived from plants or animals or combinations thereof. The sample can be processed prior to introduction into the chamber 101 or the chamber 101 can include reagents for use in such processing. In the alternative, a sample and reagent can be combined within the chamber 101. Such reagents can be used to process a sample, such as digesting solid samples with appropriate reagents such as chemicals, such as acids or bases, or with enzymes such as proteases. Other reagents can be used to extract analytes from a sample, such as extraction of antigens from biological entities, such as antigens from etiological agents such as bacteria, parasites, viruses or prions such as known in the art.

While a number of different biological specimens are suitable for collection by the present invention, commonly collected specimens are biological samples, including but not limited to fluid samples including urine, blood, serum, saliva, semen, secretions including vaginal secretions, central nervous system fluids, lavages and the like. However the specimen can also be an environmental sample, such as a sample of soil, water, wastewater, landfill or landfill leachate.

As mentioned above, the chamber 101 is expected to accommodate specimen volumes of between about 0.0001 milliliter and about 1,000 milliliters. The specimen may be diluted or concentrated depending on the concentration of the analyte and the sensitivity of the test device 500. As a general guideline the specimen may be greater than 1.0 milliliter, 0.1 milliliter, 0.01 milliliter, 0.001 milliliter or about 0.0001 milliliter and may be less than about 1 milliliter, 5 milliliters, 10 milliliters, 50 milliliters, 100 milliliters, 250 milliliters, 500 milliliters, 750 milliliters, 1,000 milliliters or about 2,000 milliliters. However, the present invention envisions additional ranges depending on the needs of the user.

Specimen Passage Slot and Reservoir Seal

A preferred aspect of the specimen collection device can include at least one specimen passage slot 200. The specimen passage slot 200 functions to make the chamber 101 and the reservoir 300 in direct fluid communication and to allow a portion of a specimen, from the specimen collected in the chamber 101 of the specimen collection device, to flow into the reservoir 300, as illustrated by the arrow in FIG. 1, and to thus make contact with the test card or test device 500 within the reservoir 300. The specimen passage slot 200 is generally in the form of an aperture positioned at about the bottom of the chamber.

The reservoir seal 306 and specimen passage slot 200 control access to the reservoir 300. As previously mentioned the specimen passage slot 200 provides access to the reservoir 300 and the reservoir seal 306 prevents excess sample from entering the reservoir 300. The reservoir seal 306 prevents excess sample from entering the reservoir 300 by trapping air or a gas within the reservoir 300. The trapped air creates a downward pressure against the sample and therefore limits the amount of sample accessible through the specimen passage slot 200. A typical urine sample will rise up to about 22 mm when the assay is conducted at about sea level.

Chamber, Reservoir and Specimen Passage Slot Configurations

As should be apparent from the above disclosure and FIG. 1, the chamber 101 and reservoir 300 can be constructed in a number of different arrangements. In one embodiment of the present invention, however, the chamber 101 and reservoir 300 form a single unit. In another embodiment of the present invention, the chamber 101 and reservoir 300 form separate units. As a refinement of the present invention and which has been previously suggested, the reservoir 300 is attachable with and is attached to the separate chamber 101. Attaching the reservoir 300 to the chamber 101 may require alignment of a chamber passage slot and a reservoir passage slot thereby resulting in a functional specimen passage slot 200. Suitable means of attaching include thermal welding, ultrasonic welding, vacuum sealing, compressing gaskets, screw mechanisms, snap couplings, gluing, compressive latching mechanisms, compressive spring mechanisms, bayonet couplings, zipping, hook and loop fasteners, screws, nails, bolting mechanisms, elastic band or bands, string and twine, wire, sliding mechanisms, compressive clips, and epoxying.

As even a further refinement of the present invention, the reservoir 300 is designed to be removable from the chamber 101. Suitable means of ensuring removability include the use of thermal welding, ultrasonic welding, vacuum sealing, compressing gaskets, screw mechanisms, snap couplings, gluing, compressive latching mechanisms, compressive spring mechanisms, bayonet couplings, zipping, hook and loop fasteners, screws, nails, bolting mechanisms, elastic band or bands, string and twine, wire, sliding mechanisms, compressive clips, and epoxying.

Test Device

The test device 500 engages the reservoir 300 and detects the presence of or measures the concentration of an analyte of interest. The test device 500 of the present invention can be of any test element known in the art and preferably comprises at least one lateral flow detection device such as a test strip. Such lateral flow detection devices include but are not limited to: immunoassays, chemical assays and enzymatic assays commonly known in the art, such as but not limited to, single antibody immunoassays, multiple antibody immunoassays, sandwich, immunoassays, competitive immunoassays, non-competitive immunoassays and the like, including assays that utilize horseradish peroxidase, alkaline phosphatase, luciferase, antibody conjugates, antibody fragments, fluorescently tagged antibodies, modified antibodies, labeled antibodies, antibodies labeled with colloidal gold, antibodies labeled with colored latex bead, and the like, which are commonly known in the art. Test devices generally involve a capture method whereby a mobile primary molecule binds the analyte and traverses the test device until a second immobilized molecule captures the bound analyte. These reactions generally occur in a reagent zone and detection zone respectively. Alternatively an enzyme and enzyme substrate may be positioned in opposing zones or the same zone. The present invention recognizes that a mobile reagent may be incorporated into a sample application zone, which may eliminate the need for a reagent zone along the test device. Results are generally provided in a detection zone. Although many devices utilize antibodies to capture analytes, any reaction that produces a detectable result on a test device is sufficient and can be incorporated into the present invention. For example and as previously mentioned enzymes bound to an analyte in the presence of a substrate may also provide a detectable result. Examples of some assay strips that may be incorporated into the present invention can be found in the following U.S. Pat. Nos. 4,857,453; 5,073,484; 5,119,831; 5,185,127; 5,275,785; 5,416,000; 5,504,013; 5,602,040; 5,622,871; 5,654,162; 5,656,503; 5,686,315; 5,766,961; 5,770,460; 5,916,815; 5,976,895; 6,248,598; 6,140,136; 6,187,269; 6,187,598; 6,228,660; 6,235,241; 6,306,642; 6,352,862; 6,372,515; 6,379,620; and 6,403,383 which are herein incorporated by reference in their entirety. Further examples of assay strips that can be incorporated into the test device and are incorporated by reference in their entirety can be found in the following U.S. patent applications Ser. Nos. 09/579,672; 09/579,673; 09/653,032; 60/233,739; 09/915,494, 10/211,199 and 09/860,408. The one or more test strips can be of any shape and dimensions, but preferably is a rectangular test strip having a sample application zone positioned generally at the bottom of the test device 500 and a detection zone positioned above the pressurized sample level. Preferably a reagent zone is positioned above the point in which a sample rises within the reservoir 300 however this need not be the case. The one or more test strips can be used separately or can be arrayed on or in a common support such as a test card.

EXAMPLE

A test device containing a test strip able to detect the presence of a drug of abuse is inserted into the reservoir. The reservoir seal is placed over the reservoir sealing the test device within the reservoir. A person in need of a drug of abuse test is given the present invention, referred to as "the urine cup" in this example. The person goes to the restroom. In the restroom, the person opens the top of the urine cup, urinates into the chamber of the urine cup, closes the urine cup, and gives the urine cup to a technician, which the technician then places on a counter. When the person urinates into the chamber of the urine cup, a portion of the urine flows into the reservoir through the specimen passage slot. The flow of urine pressurizes the air within the reservoir thereby limiting the influx of urine into the reservoir. After the urine flows into the reservoir, the urine comes into contact with the sample application zone of the test strip and migrates along the test strip. The analyte passes through the reagent zone and binds a labeled antibody. This complex continues to migrate to the detection zone where an immobilized antibody or specific binding molecule captures the analyte at a region different than the labeled antibody. The test results observable at the detection zone are viewed through the indicator windows of the test device within the sealed reservoir. The technician reports the results of the test and disposes of the used urine cup in the appropriate biohazard container.

What is claimed is:

1. A specimen collection device, comprising:
   a) a chamber, wherein said chamber is capable of collecting a specimen;
   b) a reservoir;
   c) a reservoir seal; and
   d) a specimen passage slot; wherein said chamber and said reservoir are in direct fluid communication, and further wherein said reservoir is capable of receiving a portion of said specimen from said chamber;
   whereby, upon addition of the specimen to the chamber, a portion of the specimen enters the reservoir through the specimen passage slot, the portion of the specimen entering the reservoir compresses air or a gas present in the reservoir, the compression of the gas or air limiting the amount of specimen added to the reservoir.

2. A specimen collection device, comprising:
   a) a chamber, wherein said chamber is capable of collecting a specimen;
   b) a reservoir;
   c) a specimen passage slot; wherein said chamber and said reservoir are in direct fluid communication, and further wherein said reservoir is capable of receiving a portion of said specimen from said chamber; and
   d) a reservoir seal which, in cooperation with said specimen passage slot, controls fluid access to said reservoir, wherein said reservoir seal seals said reservoir and is operable to prevent excess influx of said specimen into said reservoir upon introduction of said specimen into said chamber.

3. The device of claim 1 or 2, wherein said reservoir is configured to receive a test device.

4. The device of claim 1 or 2, wherein said reservoir is substantially transparent.

5. The device of claim 1 or 2, wherein said reservoir is constructed separately from the chamber.

6. The device of claim 1 or 2, wherein said reservoir comprises an opening which is sealed or sealed air tight with said reservoir seal.

7. The device of claim 1, wherein said reservoir seal, in cooperation with said specimen passage slot, controls fluid access to said reservoir, wherein said reservoir seal seals said reservoir and is operable to prevent excess influx of said specimen into said reservoir upon introduction of said specimen into said chamber.

8. The device of claim 1 or 2, wherein said chamber comprises a chamber seal.

9. The device of claim 3, wherein the test device is sealed inside the reservoir by the reservoir seal.

10. The device of claim 3, wherein the test device comprises at least one test strip.

11. The device of claim 1 or 2, wherein said reservoir is designed to be removable from the chamber.

12. The device of claim 1 or 2, wherein said reservoir seal is non-removable.

13. The device of claim 1 or 2, wherein said specimen is a liquid specimen.

14. The device of claim 1 or 2, wherein said specimen is urine, blood, serum or spinal fluid.

15. The device of claim 2, wherein, upon addition of the specimen to the chamber, a portion of the specimen enters the reservoir through the specimen passage slot, the portion of the specimen entering the reservoir compresses air or a gas present in the reservoir, the compression of the gas or air limiting the amount of specimen added to the reservoir.

* * * * *